United States Patent
Herfert et al.

(10) Patent No.: US 7,504,551 B2
(45) Date of Patent: *Mar. 17, 2009

(54) COLOR-STABLE SUPERABSORBENT POLYMER COMPOSITION

(75) Inventors: Norbert Herfert, Charlotte, NC (US); Michael M. Azad, Charlotte, NC (US); Peter W. Carrico, West Point, MS (US); Guy Thomas Woodrum, Suffolk, VA (US); Michael A. Mitchell, Waxhaw, NC (US); Ma-Ikay Kikama Miatudila, Monroe, NC (US)

(73) Assignee: BASF Aktiengesellschaft, Ludwigshafen (DE)

(*) Notice: Subject to any disclaimer, the term of this patent is extended or adjusted under 35 U.S.C. 154(b) by 564 days.

This patent is subject to a terminal disclaimer.

(21) Appl. No.: 10/547,353

(22) PCT Filed: Mar. 19, 2004

(86) PCT No.: PCT/EP2004/002874

§ 371 (c)(1),
(2), (4) Date: Aug. 29, 2005

(87) PCT Pub. No.: WO2004/084962

PCT Pub. Date: Oct. 7, 2004

(65) Prior Publication Data

US 2006/0089611 A1     Apr. 27, 2006

Related U.S. Application Data

(60) Provisional application No. 60/457,841, filed on Mar. 26, 2003.

(51) Int. Cl.
*A61F 13/49*     (2006.01)
*C08F 2/48*      (2006.01)
*C08F 4/40*      (2006.01)

(52) U.S. Cl. .............. 604/372; 604/358; 526/220; 526/222; 526/915; 524/815; 524/827; 524/831; 524/832; 522/42; 522/84; 522/152; 522/153; 522/154; 428/402

(58) Field of Classification Search ............. 522/42, 522/84, 152, 153, 154; 524/815, 831, 827, 524/832; 604/358, 372; 526/915, 220, 222; 428/402

See application file for complete search history.

(56) References Cited

U.S. PATENT DOCUMENTS

| | | | |
|---|---|---|---|
| 5,408,019 | A | 4/1995 | Mertens et al. |
| 5,599,335 | A | 2/1997 | Goldman et al. |
| 5,669,894 | A | 9/1997 | Goldman et al. |
| 2002/0068791 | A1 | 6/2002 | Brown et al. |

FOREIGN PATENT DOCUMENTS

| | | |
|---|---|---|
| DE | 41 23 889 | 3/1992 |
| EP | 0 290 814 | 11/1988 |
| EP | 0 942 014 | 9/1999 |
| WO | WO 00/55245 | 9/2000 |
| WO | WO 01/25289 | 4/2001 |
| WO | WO 01/55228 | 8/2001 |

*Primary Examiner*—Fred M Teskin
(74) *Attorney, Agent, or Firm*—Marshall, Gerstein & Borun LLP

(57) ABSTRACT

A color-stable superabsorbent polymer having long-term color stability, and methods of manufacturing the polymer, are disclosed. The superabsorbent polymer is prepared using a sulfinic acid derivative, like 2-hydroxy-2-sulfinatoacetic acid, a salt thereof, or a mixture thereof, as the reducing agent in a polymerization initiator system for the preparation of a superabsorbent polymer from monomers. The resulting superabsorbent polymer resists color degradation during periods of extended storage, even at an elevated temperature and humidity.

31 Claims, No Drawings

COLOR-STABLE SUPERABSORBENT POLYMER COMPOSITION

CROSS-REFERENCE TO RELATED APPLICATION

This is the U.S. national phase application of International Application No. PCT/EP2004/002874, filed Mar. 19, 2004, which claims the benefit of U.S. provisional patent application Ser. No. 60/457,841, filed Mar. 26, 2003.

FIELD OF THE INVENTION

The present invention relates to superabsorbent polymers (SAPS) having long-term color stability, and to methods of preparing the color-stable SAPs. More particularly, the present invention relates to methods of preparing a color-stable SAP using a monomer mixture containing a polymerization initiator comprising a sulfinic acid derivative, such as 2-hydroxy-2-sulfinatoacetic acid, a salt thereof, or a mixture thereof, and, optionally, subjecting the resulting SAP hydrogel to a low dose of UV radiation. The color-stable SAP can be incorporated into articles, such as bandages, diapers, sanitary napkins, and other absorbent products, wherein the SAP retains a clean, white color during extended storage periods, even under high temperature and humidity conditions.

BACKGROUND OF THE INVENTION

Water-absorbing resins are widely used in sanitary and hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are discussed generally in U.S. Pat. Nos. 5,669,894 and 5,559,335, each incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used herein, the term "SAP particles" refers to superabsorbent polymer particles in the dry state, more specifically, particles containing from no water up to about 10%, by weight, water. The terms "SAP gel," "SAP hydrogel," or "hydrogel" refer to a superabsorbent polymer containing at least about 10%, by weight, water, and typically, particles that have absorbed at least their weight in water, and more typically several times their weight in water.

SAPs have a tendency to degrade in color after long periods of storage. The tendency of an SAP to undergo a color transition from a clean, crisp, white color to a honey brown color accelerates as storage time, temperature, and humidity increase. In temperate climates, such as the United States and Europe, the rate at which an SAP undergoes color degradation is sufficiently slow such that the SAP, or article containing the SAP, typically is consumed before a color change is observable to the naked eye.

However, in tropical and subtropical climates, such as in South America and Southeast Asia, SAP color degradation is sufficiently rapid such that a color change often occurs before the SAP, or article containing the SAP, is consumed. In areas like Southeast Asia, an SAP can change color from white to honey brown in about 4 to 6 weeks. This problem is exacerbated because the SAPs may be produced far from the tropical climate, thereby increasing the time span from SAP production to use. Furthermore, consumption of articles containing an SAP in such climates is relatively low, therefore further increasing the time period between SAP production and use.

The change in color of the SAP does not affect SAP performance, but adversely affects consumer acceptance of articles containing the color-degraded SAPs. In particular, consumers observing a color-degraded SAP in a diaper form an opinion that the diaper contains a contaminant, is somehow soiled or faulty, or is of low quality. The diaper typically is returned for a refund, and the consumer is less likely to repurchase that brand of diaper.

Problems also arise at the manufacturing level because manufacturers of diapers and other articles containing an SAP refuse to incorporate a discolored SAP into their products, and return the discolored SAP to the SAP manufacturer. A color-degraded SAP, therefore, ultimately adversely affects the manufacturer of articles and the manufacturer of the SAP, who must absorb the cost of the returned goods.

It would be desirable to provide an SAP that exhibits exceptional color stability properties, such that the SAP retains its crisp, white color throughout the useful life of the SAP, or an article containing the SAP, even when stored under high temperature and humidity conditions. Furthermore, it would be desirable to provide an SAP having a long-term color stability and low residual monomer content, without adversely affecting the absorbent properties of the SAP, such as absorbing a large amount of liquids quickly, having a good fluid permeability into and through the SAP, and having a high gel strength, such that an SAP hydrogel formed from the SAP does not deform or flow under an applied stress or pressure.

Currently, SAPs, like partially neutralized, lightly crosslinked, polyacrylic acid, are manufactured using a persulfate as a component of the polymerization initiator system. A persulfate is included in the initiator system as the oxidizing agent of a redox initiator pair and to reduce the amount of residual acrylic acid monomer in the SAP to acceptable levels. A persulfate also can act as a thermal initiator. However, the persulfate further interacts with the MEHQ inhibitor present in acrylic acid monomer and imparts a low initial color to the SAP. This low initial SAP color progresses to a severe SAP discoloration over time, and especially under high temperature and humidity conditions.

The present invention is directed to overcoming the problem of SAP discoloration attributed to the presence of a color-producing oxidizing agent, like a persulfate, in the preparation of an SAP. As discussed in detail hereafter, the present invention overcomes the SAP discoloration problem (a) by utilizing a polymerization initiator system comprising a sulfinic acid derivative, such as 2-hydroxy-2-sulfinatoacetic acid, optionally 2-hydroxy-2-sulfonatoacetic acid, salts thereof, or a mixture thereof, (b) by essentially omitting a color-producing oxidizing agent from the monomer mixture, and, (c) optionally, by subjecting the SAP hydrogel resulting from the polymerization to a low dose of ultraviolet (UV) radiation.

2-Hydroxy-2-sulfinatoacetic acid disodium salt and 2-hydroxy-2-sulfonatoacetic acid disodium salt have been used as a reducing agent in a redox initiator in emulsion polymerizations. U.S. Pat. No. 5,408,019 discloses using formamidine sulfonic acid as the reducing agent in a redox initiator system.

Ultraviolet radiation previously has been used in the preparation of SAPs. For example, UV radiation has been used in conjunction with a photoinitiator to initiate polymerization of monomers and provide an SAP hydrogel, as disclosed in EP 0 290 814 B1. DE 41 23 889 A1 discloses UV irradiation of a water-absorbing resin prepared from a water-soluble polymer and a polysaccharide and/or crosslinking agent, in the presence of a radical scavenger, to provide a water-absorbing resin having a low amount of water-soluble components ($\leq 7$ wt %) and a low amount of residual monomer ($\leq 500$ ppm). The UV radiation is applied during drying or crushing of the water-absorbing resin.

PCT publication WO 01/55228 discloses subjecting a water-soluble or water-swellable polymer to UV radiation to reduce residual monomer content. An ultraviolet initiator is used in an amount of up to 10,000 ppm, by weight of monomers, preferably up to 5000 ppm, more preferably 50 to 3,000 ppm, and still more preferably 500 to 2,000 ppm. UV radiation typically is conducted for about 20 minutes.

PCT publication WO 01/25289 discloses subjecting an acrylic polymer to UV radiation after, or simultaneously with, comminuting a gelled polymer to gelled polymer particles.

In particular, the comminuted gel particles can be irradiated during a drying step in a fluid bed dryer.

SUMMARY OF THE INVENTION

The present invention is directed to a superabsorbent polymer (SAP) having long-term color stability, and to methods of manufacturing a color-stable SAP composition. More particularly, the present invention is directed to a method of preparing a color-stable SAP, without adversely affecting the fluid absorption and retention properties of the SAP particles, (a) by utilizing a polymerization initiator system comprising a sulfinic acid derivative, such as 2-hydroxy-2-sulfinatoacetic acid, optionally 2-hydroxy-2-sulfonatoacetic acid, salts thereof, or mixtures thereof, (b) by essentially omitting a coloring-forming oxidizing agent, like a persulfate, from the monomer mixture, and, optionally, (c) by subjecting the SAP hydrogel resulting from the polymerization to a low dose of UV radiation. A color-stable SAP prepared by the present method retains a crisp, clean white color over an extended storage period at a high temperature and humidity, i.e., at least 30 days when stored at 60° C. and 90% relative humidity.

One aspect of the present invention, therefore, is to provide a method of manufacturing a color-stable SAP, including the steps of (a) polymerizing a monomer mixture comprising (i) a monomer that provides an SAP, like an α,β-unsaturated carboxylic acid, such as acrylic acid, either neutralized, unneutralized, or partially neutralized, (ii) a crosslinking agent, (iii) an initiator system comprising a sulfinic acid derivative, such as 2-hydroxy-2-sulfinatoacetic acid, a salt thereof, or a mixture thereof, and that is essentially free of color-producing oxidizing agent, e.g., a persulfate, and (ivy an optional photoinitiator, to form an SAP hydrogel, (b) optionally subjecting the SAP hydrogel to a low dose of UV radiation, and (c) comminuting and drying the SAP hydrogel to provide a color-stable SAP. The resulting color-stable SAP has a low residual monomer content and maintains a crisp white color over an extended time, even under high temperature and humidity storage conditions.

Another aspect of the present invention is to provide a method of manufacturing a color-stable SAP including the steps of polymerizing a monomer mixture comprising a sulfinic acid derivative, such as 2-hydroxy-2-sulfinatoacetic acid, a salt thereof, or a mixture thereof, that provides an SAP, for example, a polymerized α,β-unsaturated carboxylic acid, to form an SAP hydrogel, optionally subjecting the SAP hydrogel to UV radiation for about 3 to about 15 minutes from a distance of about 2 to about 30 centimeters, or an equivalent UV radiation dose, comminuting the SAP hydrogel to form SAP hydrogel particles, then drying the SAP hydrogel particles to provide color-stable SAP particles. The SAP hydrogel optionally is subjected to a low dose of UV radiation, i.e., 0 to about 2000 milliwatts (mW) of UV radiation per square centimeter ($cm^2$) of SAP hydrogel. In another embodiment, the SAP hydrogel is comminuted to form SAP hydrogel particles before being subjected to UV radiation.

A sulfinic acid derivative useful in the present invention has a general structural formula:

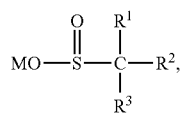

wherein M is hydrogen, an ammonium ion, or a monovalent or a divalent metal ion of groups Ia, IIa, IIb, IVa, and VIIIb of the Periodic Table of the Elements;

$R^1$ is OH or $NR^4R^5$, wherein $R^4$ and $R^5$, independently, are H or $C_1$-$C_6$alkyl;

$R^2$ is H or an alkyl, alkenyl, cycloalkyl, or aryl group, optionally having 1-3 substituents independently selected from the group consisting of $C_1$-$C_6$alkyl, OH, O—$C_1$-$C_6$alkyl, halogen, and $CF_3$; and $R^3$ is COOM, $SO_3M$, $COR^4$, $CONR^4R^5$, or $COOR^4$, wherein M, $R^4$, and $R^5$ are as defined above, or, if $R^2$ is unsubstituted or substituted aryl, $R^3$ is H;

and the salts thereof.

In preferred embodiments, the monomer mixture comprises (a) an α,β-unsaturated carboxylic acid, (b) a crosslinking agent, (b) a polymerization initiator system comprising 2-hydroxy-2-sulfinatoacetic acid, a salt thereof, or a mixture thereof, that is essentially free of a persulfate and other color-producing oxidizing agents, (d) an optional photoinitiator in an amount of 0 to about 1000 ppm by weight of α,β-unsaturated carboxylic acid and crosslinking agent, and (e) water. After drying, the color-stable SAP particles optionally are surface treated to provide surface crosslinks on the color-stable SAP particles.

Yet another aspect of the present invention is to incorporate the color-stable SAP particles into articles used to absorb liquids, for example, a diaper, a catamenial device, a feminine hygiene product, an adult incontinence product, general purpose wipes and cloths, and similar absorbent products. The articles resist color degradation over the expected life of the article, even in high temperature and humidity climates.

The above and other aspects and advantages of the present invention will become apparent from the following detailed description of the preferred embodiments of the invention, taken in conjunction with the examples and the claims.

DETAILED DESCRIPTION OF THE INVENTION

The present invention is directed to SAPs having a long-term color stability, and to methods of preparing the color-stable SAPs. The color-stable SAPs show a minor color change, to the naked eye, after storage for 30 days at 60° C. and 90% relative humidity. The present SAPs are prepared from a monomer mixture containing a polymerization initiator comprising a sulfinic acid derivative, such as 2-hydroxy-2-sulfinatoacetic acid, a salt thereof, or a mixture thereof, that is essentially free of a color-forming oxidizing agent, like a persulfate. The SAP hydrogel resulting from polymerizing the monomer mixture optionally is subjected to a low dose of UV radiation. The present polymerization initiator, and optional UV radiation, impart color stability to the SAP and reduce the amount of residual monomer in the SAP.

Suitable processes for preparing the present color-stable SAP particles include solution polymerization, also termed gel polymerization, for example, as disclosed in U.S. Pat. Nos. 4,076,663; 4,286,082; 4,654,039; and 5,145,906, each incorporated herein by reference. Another process is inverse suspension polymerization disclosed, for example, in U.S. Pat. Nos. 4,340,706; 4,497,930; 4,666,975; 4,507,438; and 4,683,274, each incorporated herein by reference.

The present disclosure is directed primarily to gel polymerization for illustrative purposes. However, the invention can be practiced using all SAP manufacturing processes, including modified bulk polymerization and inverse suspension polymerization.

In gel polymerization, SAPs are prepared from an aqueous mixture of monomers and one or more crosslinking agents to provide a water-absorbent, but water-insoluble, polymer. The aqueous monomer mixture also contains polymerization initiators, typically including a persulfate, like sodium persulfate. A persulfate has been considered an important or essential polymerization initiator ingredient in order to reduce the residual acrylic acid monomer content in SAP particles to acceptable levels.

In the typical manufacture of an SAP, the SAP is neutralized at least about 25 mole percent, more preferably at least about 50 mole percent, and usually about 70 to about 80 mole percent, to achieve optimum absorbency. Neutralization can be achieved by neutralizing the monomers before polymerization, or the polymer can be neutralized after the polymerization reaction is substantially complete. After polymerization and internal crosslinking of the monomers, followed by partial neutralization, e.g., about 50 to about 100 mole percent neutralization, preferably about 70 to about 80 mole percent neutralization, the polymer is comminuted, e.g., shredded or chopped, for more efficient drying, then dried and milled to a desired particle size. The polymer preferably then is surface treated. In embodiments wherein surface treatment is employed, a surface crosslinking agent typically is applied to the dried SAP particles. Generally, after application of the surface crosslinking agent, the SAP particles then are subjected to conditions wherein the surface crosslinking agent reacts with a portion of the SAP to crosslink the surfaces of the SAP particles.

In one embodiment of the present invention, a color-stable SAP is prepared by a method comprising the steps of (a) solution polymerizing a monomer mixture comprising (i) a monomer capable of providing an SAP polymer, like an α,β-unsaturated carboxylic acid, such as acrylic acid, either neutralized, unneutralized, or partially neutralized, (ii) a crosslinking agent, (iii) a polymerization initiator comprising a sulfinic acid derivative, such as 2-hydroxy-2-sulfinatoacetic acid, a salt thereof, or a mixture thereof, that is essentially free of a color-forming oxidizing agent, like a persulfate, (iv) an optional photoinitiator, and (v) water, to form an SAP hydrogel, (b) optionally subjecting the SAP hydrogel to a low dose of UV radiation, (c) comminuting the SAP hydrogel to form SAP hydrogel particles, (d) then drying the resulting SAP hydrogel particles, and (e) optionally surface treating the color-stable SAP particles.

The present color-stable SAPs are based on polymerized vinyl monomers, particularly α,β-unsaturated carboxylic acids, that, after polymerization, have the ability to absorb several times their weight of a liquid when crosslinked. The remainder of the specification is directed to a color-stable SAP based on acrylic acid, however, other vinyl monomers, like (meth)acrylonitrile or a (meth)acrylamide, or an ethylenic monomer having an amine substituent or a precursor to an amine substituent, e.g., N-vinyl acetamide, and other α,β-unsaturated carboxylic acids and anhydrides, also can be used in the manufacture of color-stable SAPs of the present invention. The color-stable SAPs prepared by the present methods exhibit improved color stability regardless of the identity of the monomers used to prepare the SAP, and particularly SAPs based on an α,β-unsaturated carboxylic acid or anhydride.

Accordingly, neither the chemical makeup of the color-stable SAP, nor its method of manufacture, is limited. The color-stable SAPs, therefore, can be prepared by any SAP polymerization process known in the art and can comprise an acidic water-absorbing resin (i.e., an anionic SAP), a basic water-absorbing resin (i.e., a cationic SAP), or a multicomponent SAP particle as disclosed in U.S. Pat. Nos. 6,072,101; 6,159,591; 6,222,091; and 6,329,062, each incorporated herein by reference. An extensive list of suitable SAP-forming monomers can be found in U.S. Pat. Nos. 4,076,663 and 5,149,750, each incorporated herein by reference.

Generally, acidic SAPs have carboxylate, sulfonate, sulfate, and/or phosphate groups incorporated along the polymer chain. Polymers containing these acid moieties are synthesized either from monomers previously substituted with one or more of these acidic functional groups or by incorporating the acidic functional group into the polymer after synthesis. To incorporate carboxyl groups into a polymer, any of a number of ethylenically unsaturated carboxylic acids can be homopolymerized or copolymerized. Carboxyl groups also can be incorporated into the polymer chain indirectly by hydrolyzing a homopolymer or copolymer of monomers such as acrylamide, acrylonitrile, methacrylamide, and alkyl acrylates or methacrylates. An acidic SAP can be either a strong or a weak acidic water-absorbing resin, and can be a homopolymer or a copolymer.

The acidic SAP typically is a neutralized, lightly crosslinked acrylic-type resin, such as neutralized, lightly crosslinked polyacrylic acid. The lightly crosslinked acidic SAP typically is prepared by polymerizing an acidic monomer containing an acyl moiety, e.g., acrylic acid, or a moiety capable of providing an acid group, i.e., acrylonitrile, in the presence of a crosslinking agent, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic SAP contains at least 50%, and more preferably, at least 75%, and up to 100%, acidic monomer units. The acidic resin can be unneutralized or neutralized, preferably neutralized at least 50 mole %, and most preferably at least 70 mole %, with a base prior to drying.

Ethylenically unsaturated carboxylic acid monomers, and anhydrides, amides, esters, and salts thereof, useful in the acidic SAP include, but are not limited to, acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, 2-methyl-2-butene dicarboxylic acid, maleamic acid, N-phenyl maleamide, maleamide, maleic anhydride, fumaric anhydride, itaconic anhydride, citraconic anhydride, mesaconic anhydride, methyl itaconic anhydride, ethyl maleic anhydride, diethyl maleate, methyl maleate, and maleic anhydride.

Sulfonate-containing acidic SAPs can be prepared from monomers containing functional groups hydrolyzable to the sulfonic acid form, for example, alkenyl sulfonic acid compounds and sulfoalkyl acrylate compounds. Ethylenically unsaturated sulfonic acid monomers include, but are not limited to, aliphatic or aromatic vinyl sulfonic acids, such as vinylsulfonic acid, allylsulfonic acid, vinyltoluene sulfonic acid, styrenesulfonic acid, acrylic and methacrylic sulfonic acids, such as sulfoethyl acrylate, sulfoethyl methacrylate, sulfopropyl acrylate, 2-vinyl-4-ethylbenzenesulfonic acid, 2-allylbenzenesulfonic acid, 1-phenylethylene sulfonic acid, sulfopropyl methacrylate, 2-hydroxy-3-methacryloxypropyl sulfonic acid, and 2-acrylamide-2-methylpropane sulfonic acid.

Sulfate-containing acidic SAPs are prepared by reacting homopolymers or copolymers containing hydroxyl groups or residual ethylenic unsaturation with sulfuric acid or sulfur trioxide. Examples of such sulfated polymers include sulfated polyvinyl alcohol, sulfated hydroxyethyl acrylate, and sulfated hydroxypropyl methacrylate. Phosphate-containing acidic SAPs are prepared by homopolymerizing or copolymerizing ethylenically unsaturated monomers containing a phosphoric acid moiety, such as methacryloxy ethyl phosphate.

The acidic SAP, either strongly or weakly acidic, can be any resin that acts as an SAP in its neutralized form. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The acidic SAP contains 0 to 100 percent neutralized pendant carboxylate groups (i.e., DN=0 to DN=100). Neutralization of carboxylic acid groups is accomplished using a strong organic or inorganic base, such as sodium hydroxide, potassium hydroxide, ammonia, ammonium hydroxide, or an organic amine.

Analogous to the acidic SAP, a color-stable basic SAP can be manufactured by the present method. The basic SAP can be a strong or weak basic water-absorbing resin. The strong basic resins typically are present in the hydroxide (OH) or bicarbonate ($HCO_3$) form. The basic SAP can be a single resin or a mixture of resins. The basic SAP can be a homopolymer or a copolymer.

The basic SAP, either strongly or weakly basic, therefore, can be any resin that acts as an SAP in its charged form. The basic SAP typically is a lightly crosslinked resin, such as a lightly crosslinked polyethylenimine, a poly(allylamine), a poly(allylguanidine), a poly(dimethyldiallylammonium hydroxide), a quaternized polystyrene derivative, a guanidine-modified polystyrene, a poly(vinylguanidine), or a poly(dialkylaminoalkyl (meth)acrylamide) prepared by polymerizing and lightly crosslinking a monomer having the structure

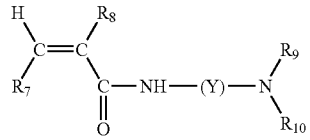

or its ester analog

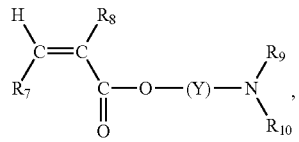

wherein $R_7$ and $R_8$, independently, are selected from the group consisting of hydrogen and methyl, Y is a divalent straight chain or branched organic radical having 1 to 8 carbon atoms, $R_9$ is hydrogen, and $R_{10}$ is hydrogen or an alkyl radical having 1 to 4 carbon atoms.

Preferred basic SAPs include a poly(vinylamine), polyethylenimine, poly(vinylguanadine), poly(methylaminoethyl acrylamide), poly(methylaminopropyl methacrylamide), or mixtures thereof. Basic SAPs are disclosed in U.S. Pat. No. 6,159,591, incorporated herein by reference. The lightly crosslinked basic SAP can contain other copolymerizable units and is crosslinked using a polyfunctional organic compound, as set forth above with respect to the acidic SAP.

Copolymerizable monomers for introduction into an acidic SAP or a basic SAP include, but are not limited to, ethylene, propylene, isobutylene, $C_{1-4}$ alkyl acrylates and methacrylates, vinyl acetate, methyl vinyl ether, and styrenic compounds having the formula:

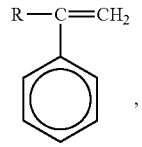

wherein R represents hydrogen or a $C_{1-6}$ alkyl group, and wherein the phenyl ring optionally is substituted with one to four $C_{1-4}$ alkyl or hydroxy groups.

Suitable $C_{1-4}$ alkyl acrylates include, but are not limited to, methyl acrylate, ethyl acrylate, isopropyl acrylate, n-propyl acrylate, n-butyl acrylate, and the like, and mixtures thereof. Suitable $C_{1-4}$ alkyl methacrylates include, but are not limited to, methyl methacrylate, ethyl methacrylate, isopropyl methacrylate, n-propylmethylmethacrylate, n-butyl methacrylate, and the like, and mixtures thereof or with $C_{1-4}$ alkyl acrylates. Suitable styrenic compounds include, but are not limited to, styrene, α-methylstyrene, p-methylstyrene, t-butyl styrene, and the like, and mixtures thereof or with $C_{1-4}$ alkyl acrylates and/or methacrylates.

As previously stated, the present invention is not limited to SAPs based on acrylic acid, but preferably extends to SAPs prepared for α,β-unsaturated carboxylic acids including, but not limited to, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride. Acrylic acid, i.e., $CH_2=CHCO_2H$, is the most preferred α,β-unsaturated carboxylic acid.

Especially preferred SAPs prepared by the present method are the alkali metal acrylate-type SAPs obtained, for example, by copolymerizing 100 parts of a monomer mixture comprising about 1 to about 50 mole percent acrylic acid, about 50 to about 99 mole percent of an alkali metal acrylate, and about 0.1 to about 5 percent by weight of an internal crosslinking agent, in an aqueous solution containing at least about 15% and up to about 60%, and preferably about 20% to about 50%, by weight, of monomers. This is a preneutralized monomer mixture. In another preferred embodiment, the alkali metal acrylate-type SAPs are obtained by first solution polymerizing acrylic acid, then neutralizing the SAP hydrogel with an alkali metal base, i.e., a postneutralization polymerization.

As set forth above, polymerization of acidic or basic monomers, and optional copolymerizable monomers, most commonly is performed by free radical processes in the presence of a polyfunctional crosslinking agent. The acidic and basic SAPs are cross-linked to a sufficient extent such that the SAP is water insoluble. Crosslinking renders the SAPs substantially water insoluble, and, in part, serves to determine the absorption capacity of the SAPs. For use in absorption applications, an acidic or basic SAP is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters, represented by the following formula (I), and bisacrylamides, represented by the following formula (II).

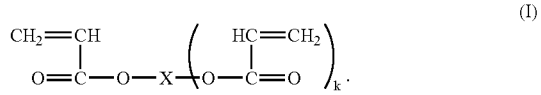

(I)

wherein X is ethylene, propylene, trimethylene, cyclohexylene, hexamethylene, 2-hydroxypropylene, $-(CH_2CH_2O)_pCH_2CH_2-$, or

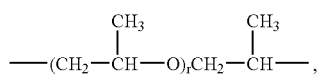

p and r each are an integer 5 to 40, and k is 1 or 2;

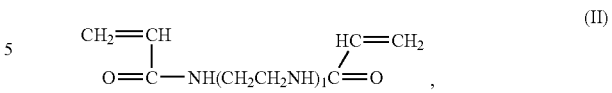

(II)

wherein l is 2 or 3.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters or a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used as crosslinking agents. Especially preferred crosslinking agents are N,N'-methylenebisacrylamide, N,N'-methylenebismethacrylamide, ethylene glycol dimethacrylate, and trimethylolpropane triacrylate.

In the preparation of a color-stable SAP of the present invention, the monomers, for example, an α,β-unsaturated carboxylic acid, and especially, acrylic acid, and crosslinking agent are subjected to a polymerization reaction in the presence of a polymerization initiator. One or more polymerization initiator is added to a mixture of the monomers and crosslinking agent to facilitate polymerization and formation of the SAP hydrogel.

Often the initiator comprises at least one thermal initiator and at least one redox initiator. Any of the various polymerization initiators that are known for use in preparing SAPs can be used in the present invention. However, in accordance with an important feature of the present invention, the polymerization initiator comprises a sulfinic acid derivative, such as 2-hydroxy-2-sulfinatoacetic acid, a salt thereof, or a mixture thereof, and is essentially free of a color-forming oxidizing agent, like a persulfate, and a color-forming reducing agent, like ascorbic acid, isoascorbic acid, and sodium erythrobate. As used herein, for color-forming reducing agents, the term "essentially free" is defined a total concentration of color-forming reducing agents of 0 ppm up to 10 ppm, by weight of the monomer mixture. For color-forming oxidizing agents, the term "essentially free" is defined as less than 500 ppm, preferably less than 300 ppm, and, and most preferably 0 ppm. In preferred embodiments, the polymerization inhibitor is free of color-forming reducing agents and color-forming oxidizing agents, especially a persulfate.

Examples of useful polymerization initiators are redox initiators comprising (a) a reducing agent comprising a sulfinic acid derivative, such as 2-hydroxy-2-sulfinatoacetic acid, a salt thereof, or a mixture thereof, and optionally, 2-hydroxy-2-sulfonatoacetic acid, a sulfite or bisulfite of an alkali metal, ammonium sulfite, ammonium bisulfite, sodium metabisulfite, a sugar, an aldehyde, a primary or secondary alcohol, and (b) an oxidizing agent, like hydrogen peroxide; an alkyl hydroperoxide, like t-butyl hydroperoxide; t-butyl perbenzoate; t-butyl peroxy isopropyl carbonate; 1,1-di-t-butylperoxy-3,3,5-trimethylcyclohexane; benzoyl peroxide, dicumyl peroxide; caprylyl peroxide; sodium peracetate; or other oxidizing agents known to persons skilled in the art. In preferred embodiments, the reducing agent is 2-hydroxy-2-sulfinatoacetic acid, and the oxidizing agent is hydrogen peroxide.

Sulfinic acid derivatives useful as the reducing agent are disclosed in U.S. Pat. No. 6,211,400, incorporated herein by reference. The sulfinic acid derivatives have a general structural formula:

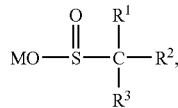

wherein M is hydrogen, an ammonium ion, or a monovalent or a divalent metal ion of groups Ia, IIa, IIb, IVa, and VIIIb of the Periodic Table of the Elements;
$R^1$ is OH or $NR^4R^5$, wherein $R^4$ and $R^5$, independently, are H or $C_1$-$C_6$alkyl;
$R^2$ is H or an alkyl, alkenyl, cycloalkyl, or aryl group, optionally having 1-3 substituents independently selected from the group consisting of $C_1$-$C_6$alkyl, OH, O—$C_1$-$C_6$alkyl, halogen, and $CF_3$; and
$R^3$ is COOM, $SO_3M$, $COR^4$, $CONR^4R^5$, or $COOR^4$, wherein M, $R^4$, and $R^5$ are as defined above, or, if $R^2$ is unsubstituted or substituted aryl, $R^3$ is H;

and the salts thereof.

In preferred embodiments, M is hydrogen, ammonium, an alkali metal ion, an alkaline earth metal ion, or zinc ion; $R^2$ is a hydrogen atom, or an alkyl or aryl group, unsubstituted or substituted, independently, with one or two hydroxyl or alkoxy substituents; and $R^3$ is COOM. Examples of useful sulfinic acid derivatives include, but are not limited to,

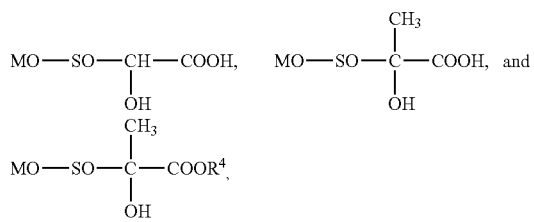

wherein M is H, Na, K, Mg, Ca, or Zn, and $R^4$ is $CH_3$ or $C_2H_5$.
2-Hydroxy-2-sulfinatoacetic acid is a reducing agent having the structure

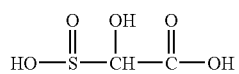

and preferably is used as a salt, such as the disodium salt, e.g.,

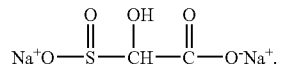

2-Hydroxy-2-sulfinatoacetic acid is available commercially in pure form as BRUGGOLITE® FF7, and also as BRUGGOLITE® FF6, both from Brüggemann Chemical, Heilbron, Germany. BRUGGOLITE® FF6 contains, by weight, 50-60% 2-hydroxy-2-sulfinatoacetic acid disodium salt, 30-35% sodium sulfite ($Na_2SO_3$), and 10-15% 2-hydroxy-2-sulfonatoacetic acid disodium salt, i.e.,

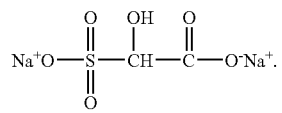

2-Hydroxy-2-sulfonatoacetic acid also performs as a reducing agent, and can be used in combination with 2-hydroxy-2-sulfinatoacetic acid.

The 2-hydroxy-2-sulfinatoacetic acid is free of formaldehyde and avoids imparting a yellow color to an SAP resulting from the solution polymerization. In addition, 2-hydroxy-2-sulfinatoacetic acid and 2-hydroxy-2-sulfonatoacetic acid decompose to the innocuous by-products sodium bisulfate, sodium formate, and carbon dioxide, thereby avoiding environmental and toxicologic problems.

A preferred redox initiator comprises 2-hydroxy-2-sulfinatoacetic acid disodium salt, 2-hydroxy-2-sulfonatoacetic acid disodium salt, or a mixture thereof, as the reducing agent, and hydrogen peroxide as the oxidizing agent, each used, for example, in an amount of about $2\times10^{-5}$ to about $2\times10^{-2}$ mole percent, based on moles of monomers (i.e., monomer and crosslinking agent) present in the monomer mixture.

The redox initiators can be used singly or in suitable combination with a thermal initiator. Examples of suitable thermal initiators are the "azo" initiators, including, but not limited to, azobisisobutyronitrile; 4-t-butylazo-4'-cyanovaleric acid; 4,4'-azobis(4-cyanovaleric acid); 2,2'-azobis(2-amidinopropane) dihydrochloride; 2,2'-azobis(2,4-dimethylvaleronitrile); dimethyl 2,2'-azobisisobutyrate; 2,2'-azodimethyl bis(2,4-dimethylvaleronitrile); (1-phenylethyl)azodiphenylmethane; 2,2'-azobis(2-methylbutyronitrile); 1,1'-azobis(1-cyclohexanecarbonitrile); 2-(carbamoylazo)isobutyronitrile; 2,2'-azobis(2,4,4-trimethylpenta-2-phenylazo-2,4-dimethyl-4-methoxyvaleronitrile; 2,2'-azo-bis(2-methylpropane); 2,2'-azobis(N,N'dimethyleneisobutyramidine) dihydrochloride; 4,4'azobis(4-cyanopentanoic acid); 2,2'-azobis(2-methyl-N-[1,1-bis(hydroxymethyl)-2-hydroxyethyl] propionamide); 2,2'-azobis(2-methyl-N-[1,1-bis(hydroxymethyl)ethyl]propionamide); 2,2'-azobis[2-methyl-N(2-hydroxyethyl)propionamide]; 2,2'-azobis(isobutyramide) dihydrate; and other thermal initiators known to persons skilled in the art.

Especially preferred polymerization initiators comprise (a) a redox initiator comprising (i) hydrogen peroxide as an oxidizing agent and (ii) 2-hydroxy-2-sulfinatoacetic acid, optionally 2-hydroxy-2-sulfonatoacetic acid, salts thereof, or a mixture thereof as the reducing agent, and (b) an azo initiator, such as azobisisobutyronitrile or 2,2'-azobis(2amidinopropane) dihydrochloride. A preferred thermal initiator for use in the present method is 2,2'-azobis(2-amidinopropane) dihydrochloride, commercially available under the tradename V-50 from Wako Chemicals U.S.A., Inc., Richmond, Va. The initiator typically is used in an aqueous solution, but the initiator can be diluted with another suitable solvent.

In addition to the polymerizable monomer, crosslinking agent, and polymerization initiator, a monomer mixture used in the method of the present invention optionally contains a photoinitiator. The photoinitiator is present in the monomer mixture in a low amount, in particular, in an amount of 0 to about 1000 ppm, by weight of monomers and cross-linking agent, and preferably about 10 to about 500 ppm. To achieve the full advantage of the present invention, the photoinitiator is present in the monomer mixture in an amount of about 15 to about 300 ppm, by weight of monomers and crosslinking agent.

The photoinitiator is present to assist in reducing the residual acrylic acid monomer in the SAP. In prior methods of manufacturing an SAP, a persulfate was utilized as a component of the redox initiator, or as a thermal initiator, to initiate the polymerization reaction and to reduce the amount of residual acrylic acid monomer in the SAP. However, a persulfate interacts with the MEHQ inhibitor present in acrylic acid monomer and provides a slightly colored SAP. This color increases over time, and especially in hot, humid conditions, to provide an unacceptable, honey-brown colored SAP.

In accordance with an important feature of the present invention, the monomer mixture is essentially free of a color-producing oxidizing agent, especially a persulfate. The photoinitiator, in combination with a low dose of UV radiation, then serves to reduce the amount of residual acrylic acid monomer in the SAP, i.e., to below 500, and preferably below 400 ppm by weight of the SAP, that previously was accomplished using a persulfate.

The identity of the photoinitiator is not limited, but is inert (i.e., is not decomposed) under polymerization conditions. A preferred photoinitiator has a structure

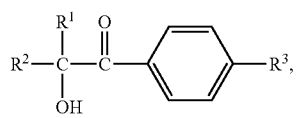

wherein $R^1$ and $R^2$, independently, are $C_{1-3}$ alkyl, or are taken together to form a $C_{4-8}$ carbocyclic ring, $R^3$ is H, methyl, ethyl, or $(OCH_2CH_2)_nOH$, and n is 1-20.

Specific photoinitiators include, but are not limited to,

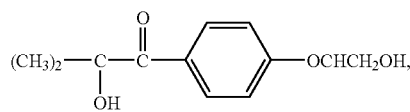

i.e., 1-(4-(2-hydroxyethyl)phenyl)-2-hydroxyl-2-methyl-1-propane-1-one, available as IRGACURE® 2959 from Ciba Specialty Chemicals, Hawthorne, N.Y.;

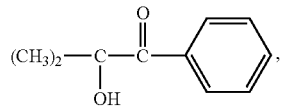

i.e., 1-phenyl-2-hydroxy-2-methyl-1-propane-1-one, also available from Ciba Specialty Chemicals as DAROCUR® 1173;

hydroxycyclohexyl phenyl ketone, available from Ciba Chemical Specialties as IRGACURE® 184;

2,2-dimethoxy-1,2-diphenylethan-1-one, available from Ciba Specialty Chemicals as IRGACURE® 651;

and mixtures thereof.

Additional useful photoinitiators include, but are not limited to, benzoin, benzoin ethers, benzyl ketals, acylphosphine oxides, camphorquinone, bisimidazole, a dialkylacetophenone, an α-aminoacetophenone, a chlorinated acetophenone, benzophenone, a benzophenone derivative (for example, p-benzoylbenzyl trimethyl ammonium bromide), a thioxanthone derivative (for example, (3-(3,4-dimethyl-9-oxo-9H-thioxanthen-2-yloxy)-2-hydroxypropyl) trimethyl ammonium chloride), and mixtures thereof.

In addition to the monomers, crosslinking agent, polymerization initiators, and photoinitiator, the monomer mixture contains water. Generally, the monomer mixture contains about 40 to about 80 percent, more preferably about 50 to about 70 percent, water, by weight of the monomer mixture.

The monomers present in monomer mixture are crosslinked concurrently with aqueous solution polymerization to a sufficient extent such that the resulting SAP is water insoluble, but has an ability to absorb several times its weight in water to form an SAP hydrogel. In many cases, after comminuting and drying of the SAP hydrogel, the resulting SAP is surface treated. Surface treatment results in surface crosslinking of the SAP particles. Surface treating an SAP enhances the ability of the SAP to absorb and retain aqueous media under a load.

As understood in the art, a surface-treated SAP particle has a higher level of cross-linking in the vicinity of the particle surface than in the particle interior. As used herein, "surface" describes the outer-facing boundaries of the SAP particle. For porous SAP particles, exposed internal surfaces also are included in the definition of surface.

In general, surface treating is achieved by contacting an SAP with a solution of a surface crosslinking agent to wet the outer surfaces of the SAP particles. Surface crosslinking and drying of the SAP particles then are performed, preferably by heating at least the wetted surfaces of the SAP particles. Surface treating also can be achieved by "annealing" (i.e., heating) the SAP particles at a sufficient temperature for a sufficient time to provide surface crosslinks.

Typically, a solution of a surface crosslinking agent contains about 0.01% to about 4%, and preferably about 0.4% to about 2%, by weight, surface crosslinking agent in a suitable solvent, for example, water or an alcohol. The solution can be applied as a fine spray onto the surface of freely tumbling SAP particles at a ratio of about 1:0.01 to about 1:0.5 parts by weight SAP particles to solution of surface crosslinking agent. The surface crosslinker is present in an amount of 0.001% to about 5%, and preferably 0.005% to about 0.5%, by weight of the SAP particles. To achieve the full advantage of the present invention, the surface crosslinker is present in an amount of about 0.01% to about 0.4%, by weight.

The crosslinking reaction and drying of the surface-treated SAP particles are achieved by heating the surface-treated polymer at a suitable temperature, e.g., about 105° C. to about 200° C., and preferably about 105° C. to about 180° C. However, any other method of reacting the crosslinking agent to achieve surface crosslinking of the SAP particles, and any other method of drying the SAP particles, like microwave energy or the such, can be used.

Suitable surface crosslinking agents possess sufficient reactivity such that crosslinking occurs in a controlled fashion, preferably at a temperature of about 25° C. to about 180° C. Nonlimiting examples of suitable surface crosslinking agents include:

(a) polyhydroxy compounds, such as glycols and glycerol;
(b) metal salts;
(c) quaternary ammonium compounds;
(d) a multifunctional epoxy compound, for example, ethylene glycol diglycidyl ether, bisphenol A diglycidyl ether, and bisphenol F diglycidyl ether;
(e) an alkylene carbonate, such as ethylene carbonate or propylene carbonate;
(f) a polyaziridine, such as 2,2-bishydroxymethyl butanol tris[3(1-aziridine propionate)];
(g) a haloepoxy, such as epichlorohydrin;
(h) a polyamine, such as ethylenediamine;
(i) a polyisocyanate, such as toluene diisocyanate, isophorone diisocyanate, methylene diisocyanate, xylene diisocyanate, and hexamethylene diisocyanate;
(j) dihalides and disulfonate esters, for example, compounds of the formula $Y-(CH_2)_p-Y$, wherein p is a number from 2 to 12, and Y, independently, is halo (preferably bromo), tosylate, mesylate, or other alkyl or aryl sulfonate esters;
(k) multifunctional aldehydes, for example, glutaraldehyde, trioxane, paraformaldehyde, terephthaldehyde, malonaldehyde, and glyoxal, and acetals and bisulfites thereof;
(l) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;
(m) organic titanates, such as TYZOR AA, available from E.I. DuPont de Nemours, Wilmington, Del.;
(n) melamine resins, such as the CYMEL resins available from Cytec Industries, Wayne, N.J.;
(o) hydroxymethyl ureas, such as N,N'-dihydroxymethyl-4,5-dihydroxyethylene urea;
(p) a hydroxyalkylamide (HAA), for example, as disclosed in U.S. Pat. No. 6,239,230, incorporated herein by reference, but not limited to, bis[N,N-di(β-hydroxyethyl)] adipamide, bis[N,N-di(β-hydroxypropyl)] succinamide, bis[N,N-di(β-hydroxyethyl)] azelamide, bis[N—N-di(β-hydroxypropyl)] adipamide, and bis[N-methyl-N-(β-hydroxyethyl)] oxamide. A commercially available β-HAA is PRIMID™ XL-552 from EMS-CHEMIE, Domat, Switzerland. Another commercially available HAA is PRIMID™ QM-1260 from EMS-CHEMIE;
(q) 2-oxazolidinone and derivatives thereof; and
(r) other crosslinking agents for SAPs known to persons skilled in the art.

A preferred surface crosslinking agent comprises an HAA, ethylene glycol diglycidyl ether (EGDGE), propylene glycol, or mixtures thereof.

It is theorized, but not relied upon herein, that inhibitors, which are added to the vinyl monomers to prevent premature polymerization during transport and storage, and which are present in the SAP polymer, are slowly oxidized by a persulfate causing the color of the SAP to degrade from white to honey brown. This color change occurs at a faster rate at elevated temperatures and relative humidity.

For example, the monomethyl ether of hydroquinone (MEHQ) is the inhibitor typically used to prevent the premature polymerization of acrylic monomers used in the manufacture of the SAPs, like acrylic acid and the crosslinking agents. Typically, the amount of inhibitor, like MEHQ, added to the monomer is about 15 to about 200 ppm. The inhibitors are not consumed during polymerization and are present in the SAP hydrogel after polymerization of the monomers. The color change of the SAP is theorized to result from oxidation of an inhibitor, like MEHQ, by a persulfate, or other color-forming reducing agent, to a quinone.

To prevent color degradation of an SAP to a consumer-unacceptable honey brown color, a monomer mixture used to provide an SAP comprises a sulfinic acid derivative, preferably 2-hydroxy-2-sulfinatoacetic acid, optionally 2-hydroxy-2-sulfonatoacetic acid, salts thereof, or a mixture, thereof, as a reducing agent of the redox initiator, is essentially free of a persulfate, and optionally includes about 10 to about 1000 ppm of a photoinitiator. By using a monomer mixture essentially free of a persulfate, the resulting SAP has a crisp, white color, and the white color of the resulting SAP is stabilized and preserved. The optional photoinitiator is present in the monomer mixture to assist in reducing the amount of free monomer in the SAP.

Therefore, the present invention is directed to a method of manufacturing an SAP that improves the color, and avoids discoloration, of SAPs. The interaction between sodium persulfate and the MEHQ inhibitor results in a low initial SAP color and additional SAP discoloration during storage, especially under hot and humid conditions. To date, sodium persulfate has been an important, or a necessary, ingredient in the monomer mixture to reduce the residual acrylic acid content in the SAP to a consumer-acceptable level.

It now has been found that the monomer mixture can be essentially free of a persulfate, and a redox initiator of the present invention, in combination with the optional thermal initiator, optional photoinitiator, and optional UV radiation dose, can be used to reduce residual acrylic acid in a color-stable SAP. In one particular embodiment of the present invention, a low dose of UV radiation can be administered at the end of the polymerization, i.e., after a majority of the acrylic acid monomer has been converted to an SAP hydrogel and the water content of the hydrogel preferably has been reduced to about 25 wt % or less. In accordance with the present invention, unexpectedly low residual acrylic acid levels are achieved and the initial color and long-term color of the SAP are improved considerably.

In particular, a monomer mixture is formed by admixing the monomers, crosslinking agent, polymerization initiators, optional photoinitiator, and water. Although the order of admixing these materials is not particularly important, it is preferred to add the initiators last for safety reasons. The amounts of the individual components of the monomer mixture are set forth above.

The monomer mixture then is subjected to conditions under which the monomers and crosslinking agents polymerize to form an SAP hydrogel. The conditions can be static or continuous, for example, by applying the monomer mixture to a moving conveyor that passes through a heating zone that initiates the polymerization reaction. After polymerization on the conveyor, the resulting SAP hydrogel optionally advances to a UV zone, wherein an optional low dose of UV radiation is applied to the SAP hydrogel. The SAP hydrogel also is subjected to a mechanical comminution, i.e., reduction of the SAP hydrogel to SAP hydrogel particles, for example, by chopping, prior to or after optional UV treatment. Preferably, the SAP hydrogel is comminuted after the optional UV treatment.

The SAP hydrogel, if not previously neutralized, can be neutralized with a base, for example, with sodium carbonate, to provide an SAP hydrogel having a degree of neutralization (DN) of about 50 to about 100, preferably about 65 to about 85, more preferably about 75 to about 80. This postneutralization step, if necessary, can be performed before or after the SAP hydrogel optionally is irradiated. Preferably, the monomers are neutralized prior to polymerization.

Drying of the SAP hydrogel provides a color-stable SAP of the present invention. The dehydration step can be performed by heating the SAP hydrogel at a temperature of about 120° C. for about 1 to about 2 hours in a forced-air oven or by heating the SAP hydrogel overnight at a temperature of about 60° C. The dried SAP optionally then can be surface crosslinked with a surface crosslinker, like ethylene glycol diglycidyl ether or an HAA, for example.

The SAP hydrogel optionally is subjected to a low dose of UV radiation intensity, for example, 2000 milliwatt/cm$^2$ or less, preferably 500 milliwatt/cm$^2$ or less, and to achieve the full advantage of the present invention, about 5 to about 200 milliwatt/cm$^2$.

The UV radiation dose generally is administered using a UV lamp with an intensity of about 100 to about 700 watts per inch (W/in), preferably about 400 to about 600 W/in, for 0.1 seconds to 10 minutes, with the distance between the UV lamp and the SAP hydrogel being 2 to 30 centimeters. UV radiation can be conducted under vacuum, in the presence of an inorganic gas, such as nitrogen, argon, helium, and the like, or in air. Suitable UV sources include a UV flood system from Starna or a Solartell Solarscope, Model 1, with a multidirectional probe.

Particles of a color-stable SAP of the present invention can be in any form, either regular or irregular, such as granules, fibers, beads, powders, flakes, or foams, or any other desired shape, such as a sheet. In embodiments wherein the color-stable SAP is prepared using an extrusion step, the shape of the SAP is determined by the shape of the extrusion die. The shape of the color-stable SAP particles also can be determined by other physical operations, such as milling.

In one embodiment, the particles of the color-stable SAP are in the form of a granule or a bead, having a particle size of about 10 to about 10,000 microns (μm), and preferably about 100 to about 1,000 μm. To achieve the full advantage of the present invention, the particles of the color-stable SAP have a particle size of about 150 to about 800 μm.

In another embodiment, the particles of the color-stable SAP are in the shape of a fiber, i.e., an elongated, acicular particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. Polyacrylic acid is about 4 decitex.

Cylindrical fibers of a color-stable SAP have a minor dimension (i.e., diameter of the fiber) less than about 1 mm, usually less than about 500 μm, and preferably less than 250 μm, down to about 50 μm. The cylindrical fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

The method of the present invention also can be used in the preparation of a multi-component SAP, as disclosed in U.S. Pat. Nos. 6,072,101; 6,159,591; 6,222,091; and 6,329,062, each incorporated herein by reference.

A color-stable SAP of the present invention has an outstanding water-absorbing ability, and is useful for use in sanitary goods, paper diapers, disposable diapers and similar hygienic goods, agricultural or horticultural water-retaining agents, industrial dehydrating agents, sludge coagulants, thickening agents, condensation preventing agents for building materials, release control agents for chemicals and various other applications. Furthermore, a present color-stable SAP retains its white color over extended storage periods at elevated temperature and relative humidity. The present color-stable SAP particles, therefore, are useful in articles, like diapers, having improved consumer appeal.

After storage at 60° C. and 90% relative humidity for 30 days, a color-stable SAP of the present invention has an HC60 color value of at least 60 and a maximum b-value of 10. To achieve the full advantage of the present invention, the color-stable SAP exhibits an HC60 color value of at least 63 and a maximum b-value of 8 after storage at 60° C. and 90% relative humidity for 30 days.

EXAMPLES

The following illustrate nonlimiting examples of the present invention, and are not intended to limit the scope thereof.

Test Methods

Centrifuge Retention Capacity (CRC)

The CRC (centrifuge retention capacity) test is designed to measure the amount of 0.9% saline solution retained inside an SAP under a specific centrifuge force. Measurement of CRC is disclosed in U.S. Pat. No. 6,187,828 and U.S. Pat. No. 5,633,316, each incorporated herein by reference.

Absorbency Under Load (AUL)

The AUL (absorbency under load) test is designed to measure the ability of an SAP to absorb a fluid under load. Measurement of AUL is disclosed in U.S. Pat. No. 6,187,828 and U.S. Pat. No. 5,633,316, each incorporated herein by reference.

Extractables

The extractable content of an SAP is determined by mixing 1.0 g of the SAP with 200 mL of a 0.9% saline solution in a 250 mL beaker containing a magnetic stirrer bar, then stirring the solution at 500 rpm for 16 hours. The entire solution then is filtered. Fifty mL of the filtrate then is withdrawn, and the free acid groups of the polymer material dissolved in the filtrate are titrated to pH 10 using a 0.1 mol/L NaOH solution. The resulting solution then is titrated to pH 2.7 using a 0.1 mol/L HCl solution to determine the concentration of neutralized acrylates. The titration data are used to calculate the total amount of extractable polymer present in the SAP, using a 0.9% saline solution as blank:

$V_a$=ml of base required to titrate the sample aliquot to pH 10.0
$V_{ab}$=ml of base required to titrate the blank to pH 10.0
$V_b$=ml of acid required to titrate the sample aliquot to pH 2.7
$V_{bb}$=ml of acid required to titrate the blank to pH 2.7
$C_a$=molar concentration of base (0.1 mol/L NaOH)
$C_b$=molar concentration of acid (0.1 mol/L HCl)
$M_a$=relative molar mass of acrylic acid, 72 g/mol
$M_b$=relative molar mass of sodium acrylate, 94 g/mol
D=dilution factor, 200/50=4
m=mass of sample in g.

The amount of acrylic acid (e.g., polyacrylic acid) in the supernatant aliquot ($N_a$) is given by:

$$N_a=(V_a-V_{ab})\times(C_a/1000) \text{ (moles)}$$

The total amount of acrylate in the supernatant aliquot ($N_1$) is given by:

$$N_1=(V_b-V_{bb})\times(C_b/1000) \text{ (moles)}$$

The amount of neutralized acrylate in the supernatant aliqot ($N_b$) is given by:

$$N_b=N_1-N_a \text{ (moles)}$$

The relative amounts of acrylate acid groups ($W_a$) and sodium acrylate groups ($W_b$) are given by:

$$W_a=N_a\times M_a\times D(g)$$

$$W_b=N_b\times M_b\times D(g)$$

The extractable content (W) of the superabsorbent polymer is given by:

$$W=((W_a+W_b)/m)\times 100\%(\%).$$

Residual Acrylic Acid

One gram (1 g) of SAP is weighed into a 250 mL beaker. Two hundred mL of 0.9% saline solution are added, a stir bar is placed in the beaker, the beaker is covered with parafilm, then the mixture is stirred at 500 rpm for 1 hour. After 1 hour, the sample is allowed to settle for 5 minutes and the supernatant is filtered using a 3 cc sterile syringe and 0.45 μm filter. The content of acrylic acid is measured by HPLC analysis using 0.1 N sulfuric acid as mobile phase and UV detection (210 nm).

Hunter Color (HC60) and b-Value

This test procedure is a method of measuring the perceived color of polymer related to its spectral characteristics. Spectral characteristics are specified by reflectance (or transmittance) as a function of wavelength. The measurement is performed on the polymer powder using a MACBETH Color-Eye 2180 Spectrophotometer according to the manufacturer's instructions, using a reflection cuvette or 35×10 mm petri dish with lid as a sample cell.

In this system,

"L" is a measure of the lightness of a sample, and ranges from 0 (black) to 100 (white), "b" is a measure of yellowness (positive b-values) or blueness (negative b-values), Hunter Color HC60 is defined as: HC60=L−3b.

Example 1

An aqueous monomer mixture containing 25.6 wt. % sodium acrylate, 7.4 wt. % acrylic acid, 0.4 wt. % ethoxylated trimethylol propane triacrylate based on monomer (i.e., sodium acrylate plus acrylic acid), 0.025 wt. % 2-hydroxy-2-methyl-1-phenyl-propan-1-one (DAROCUR® 1173) based on monomer, 0.008 wt. % 2,2-dimethoxy-1,2-diphenylethan-1-one (IRGACURE® 651) based on monomer, and 0.02 wt. % a mixture containing 50-60% 2-hydroxy-2-sulfinatoacetic acid, disodium salt, 30-35% sodium sulfite, and 10-15% 2-hydroxy-2-sulfonatoacetic acid, disodium salt (BRUGGOLITE® FF6) based on monomer was prepared. The mixture was cooled to 15° C. and deoxygenated by bubbling a nitrogen stream through the mixture. Polymerization of the resulting monomer mixture then was initiated by addition of 0.04 wt. % hydrogen peroxide based on monomer and, after 5 minutes, the mixture was placed under a UV light (UV intensity=20 mW/cm²) for 15 minutes. The resulting gel was extruded three times through a KitchenAid Model K5SS mixer fitted with a meat grinder attachment. The gel was dried at 150° C. for one hour, then milled and sized to 150-850 μm. The dry powder then was surface crosslinked by spraying a solution, containing 0.1 wt. % ethylene glycol diglycidyl ether based on powder, 3.35 wt. % water based on powder and 1.65 wt. % propylene glycol based on powder onto the powder particles, followed by curing at 150° C. for one hour. The properties of the resulting polymer were as follows:

| | |
|---|---|
| CRC = | 33.2 g/g |
| AUL 0.7 psi = | 24.9 g/g |
| Extractables = | 9.8 wt. % |
| Residual acrylic acid = | 360 ppm |
| Hunter Color, HC60, initial = | 85 |
| Hunter Color, HC60, after 30 days @60° C./90% relative humidity = | 75 |
| Hunter Color, b-value, initial = | 2.6 |
| Hunter Color, b-value, after 30 days @60° C./90% relative humidity = | 3.8. |

Comparative Example 1

An aqueous monomer mixture containing 25.6 wt. % sodium acrylate, 7.4 wt. % acrylic acid, 0.4 wt. % ethoxylated trimethylolpropane triacrylate based on monomer, 0.025 wt. % 2-hydroxy-2-methyl-1-phenyl-propan-1-one (DAROCUR® 1173) based on monomer, 0.008 wt. % 2,2-dimethoxy-1,2-diphenylethan-1-one (IRGACURE® 651) based on monomer, and 0.02 wt. % ascorbic acid based on monomer was prepared. The mixture was cooled to 15° C. and deoxygenated by bubbling a nitrogen stream through the mixture. Polymerization of the resulting monomer mixture then was initiated by addition of 0.04 wt. % hydrogen peroxide based on monomer and, after 5 minutes, the mixture was placed under a UV light (UV intensity=20 mW/cm²) for 15 minutes. The resulting gel was extruded three times through a KitchenAid Model K5SS mixer fitted with a meat grinder attachment. The gel then was dried at 150° C. for one hour, then milled and sized to 150-850 μm. The dry powder then was surface crosslinked by spraying a solution containing 0.1 wt. % ethylene glycol diglycidyl ether based on powder, 3.35 wt. % water based on powder, and 1.65 wt. % propylene glycol based on powder onto the powder particles, followed by curing at 150° C. for one hour. The properties of the resulting polymer were as follows:

| | |
|---|---|
| CRC = | 33.4 g/g |
| AUL 0.7 psi = | 23.5 g/g |
| Extractables = | 11.5 wt. % |
| Residual acrylic acid = | 420 ppm |
| Hunter Color, HC60, initial = | 67 |
| Hunter Color, HC60, after 30 days @60° C./90% relative humidity = | 51 |
| Hunter Color, b-value, initial = | 6.4 |
| Hunter Color, b-value, after 30 days @60° C./90% relative humidity = | 12.5. |

Comparative Example 2

An aqueous monomer mixture containing 25.6 wt. % sodium acrylate, 7.4 wt. % acrylic acid, 0.4 wt. % ethoxylated trimethylolpropane triacrylate based on monomer, 0.025 wt. % 2-hydroxy-2-methyl-1-phenyl-propan-1-one (DAROCUR® 1173) based on monomer, 0.008 wt. % 2,2- dimethoxy-1,2-diphenylethan-1-one (IRGACURE® 651) based on monomer, and 0.25 wt. % sodium persulfate based on monomer was prepared. The mixture was cooled to 15° C. and deoxygenated by bubbling a nitrogen stream through the mixture. Polymerization of the resulting monomer mixture then was initiated by placing it under a UV light (UV intensity=20 mW/cm$^2$) for 20 minutes. The resulting gel was extruded three times through a KitchenAid Model K5SS mixer fitted with a meat grinder attachment. The gel was dried at 150° C. for one hour, then milled and sized to 150-850 μm. The dry powder then was surface crosslinked by spraying a solution containing 0.1 wt. % ethylene glycol diglycidyl ether based on powder, 3.35 wt. % water based on powder, and 1.65 wt. % propylene glycol based on powder onto the powder particles, followed by curing at 150° C. for one hour. The properties of the resulting polymer were as follows:

| | |
|---|---|
| CRC = | 31.5 g/g |
| AUL 0.7 psi = | 23.2 g/g |
| Extractables = | 13.6 wt. % |
| Residual acrylic acid = | 280 ppm |
| Hunter Color, HC60, initial = | 55 |
| Hunter Color, HC60, after 30 days @60° C./90% relative humidity = | 35 |
| Hunter Color, b-value, initial = | 9.5 |
| Hunter Color, b-value, after 30 days @60° C./90% relative humidity = | 14.8. |

Comparative Example 3

An aqueous monomer mixture containing 25.6 wt. % sodium acrylate, 7.4 wt. % acrylic acid, 0.4 wt. % ethoxylated trimethylolpropane triacrylate based on monomer, 0.025 wt. % 2-hydroxy-2-methyl-1-phenyl-propan-1-one (DAROCUR® 1173) based on monomer, 0.008 wt. % 2,2-dimethoxy-1,2-diphenylethan-1-one (IRGACURE® 651) based on monomer, and 0.15 wt. % 2,2'-azobisamidinopropane dihydrochloride based on monomer was prepared. The mixture was cooled to 15° C. and deoxygenated by bubbling a nitrogen stream through the mixture. Polymerization of the resulting monomer mixture then was initiated by placing the mixture under a UV light (UV intensity=20 mW/cm$^2$) for 20 minutes. The resulting gel was extruded three times through a KitchenAid Model K5SS mixer fitted with a meat grinder attachment. The gel was dried at 150° C. for one hour, then milled and sized to 150-850 μm. The dry powder then was surface cross-linked by spraying a solution containing of 0.1 wt. % ethylene glycol diglycidyl ether based on powder, 3.35 wt. % water based on powder and 1.65 wt. % propylene glycol based on powder onto the powder particles, followed by curing at 150° C. for one hour. The properties of the resulting polymer were followed by:

| | |
|---|---|
| CRC = | 32.6 g/g |
| AUL 0.7 psi = | 22.8 g/g |
| Extractables = | 12.9 wt. % |
| Residual acrylic acid = | 3580 ppm |
| Hunter Color, HC60, initial = | 87 |
| Hunter Color, HC60, after 30 days @60° C./90% relative humidity = | 77 |
| Hunter Color, b-value, initial = | 2.3 |
| Hunter Color, b-value, after 30 days @60° C./90% relative humidity = | 4.1. |

Example 1 and Comparative Examples 1-3 each are pre-neutralization polymerizations, and illustrate unexpected benefits provided by the present invention. Example 1, which utilized BRUGGOLIT® FF6 as a reducing agent, provides an SAP having excellent properties, especially with respect to residual acrylic acid (RAA), extractables, and HC60 and b-values (both initial and after 30 days at 60° C. and 90% relative humidity). Comparative Example 1, which utilized ascorbic acid as a reducing agent, showed a substantial adverse effect on color (i.e., HC60 value and b-value after 30 days at 60° C. and 90% relative humidity), and increased extractables and RAA compared to Example 1. Comparative Example 2 utilized sodium persulfate, and demonstrated a very poor initial color and substantial color degradation (i.e., HC60 value and b-values), and a substantial increase in RM compared to Example 1. Comparative Example 3 utilized only a thermal initiator, and although the initial color and color stability was good, the RM was unacceptable for commercial applications and the extractables increased substantially compared to Example 1.

Example 2

An aqueous monomer mixture containing 28 wt. % acrylic acid, 0.2 wt. % pentaerythritol triallyl ether based on acrylic acid, 0.025 wt. % sodium persulfate based on acrylic acid, 0.044 wt. % 2-hydroxy-2-methyl-1-phenyl-propan-1-one (DAROCUR® 1173) based on acrylic acid, 0.022 wt. % 2,2-dimethoxy-1,2-diphenylethan-1-one (IRGACURE® 651), and 0.025 wt. % 2-hydroxy-2-sulfinatoacetic acid, disodium salt (BRUGGOLITE® FF7) was prepared. The mixture was cooled to 15° C. and deoxygenated by bubbling a nitrogen stream through the mixture. Polymerization of the resulting monomer mixture then was initiated by addition of 0.05 wt. % hydrogen peroxide based on monomer and, after 5 minutes, the mixture was placed under a UV light (UV intensity=20 mW/cm$^2$) for 20 minutes. The resulting polyacrylic acid gel was extruded through a KitchenAid Model K5SS mixer fitted with a meat grinder attachment. Next, sodium carbonate was added to the hydrogel, to adjust the neutralization degree of the acrylic acid groups to 75 mol % followed by two additional extrusions. The gel was dried at 150° C. for one hour, then milled and sized to 150-850 μm. The dry powder then was surface crosslinked by spraying a solution containing 0.15 wt. % ethylene glycol diglycidyl ether based on powder, 3.35 wt. % water based on powder, and 8.0 wt. % methanol based on powder onto the powder particles, followed by curing at 150° C. for one hour. The properties of the resulting polymer were as follows:

| | |
|---|---|
| CRC = | 30.4 g/g |
| AUL 0.7 psi = | 25.8 g/g |
| Extractables = | 8.2 wt. % |
| Residual acrylic acid = | 290 ppm |
| Hunter Color, HC60, initial = | 74 |
| Hunter Color, HC60, after 30 days @60° C./90% relative humidity = | 66 |
| Hunter Color, b-value, initial = | 3.9 |
| Hunter Color, b-value, after 30 days @60° C./90% relative humidity = | 5.7. |

Comparative Example 4

An aqueous monomer mixture containing 28 wt. % acrylic acid, 0.2 wt. % pentaerythritol triallyl ether based on acrylic acid, 0.025 wt. % sodium persulfate based on acrylic acid, 0.044 wt. % 2-hydroxy-2-methyl-1-phenyl-propan-1-one (DAROCUR® 1.173) based on acrylic acid, 0.022 wt. %

2,2-dimethoxy-1,2-diphenylethan-1-one (IRGACURE® 651) and 0.025 wt. % ascorbic acid was prepared. The mixture was cooled to 15° C. and deoxygenated by bubbling a nitrogen stream through the mixture. Polymerization of the resulting monomer mixture then was initiated by addition of 0.05 wt. % hydrogen peroxide based on monomer and, after 5 minutes, the mixture was placed under a UV light (UV intensity=20 mW/cm$^2$) for 20 minutes. The resulting polyacrylic acid gel was extruded through a KitchenAid Model K5SS mixer fitted with a meat grinder attachment. Next, sodium carbonate was added to the hydrogel to adjust the neutralization degree of the acrylic acid groups to 75 mol %, followed by two additional extrusions. The gel was dried at 150° C. for one hour, then milled and sized to 150-850 μm. The dry powder then was surface crosslinked by spraying a solution containing 0.15 wt. % ethylene glycol diglycidyl ether based on powder, 3.35 wt. % water based on powder, 8.0 wt. % methanol based on powder onto the powder particles, followed by curing at 150° C. for one hour. The properties of the resulting polymer were as follows:

| | |
|---|---|
| CRC = | 30.2 g/g |
| AUL 0.7 psi = | 25.4 g/g |
| Extractables = | 8.7 wt. % |
| Residual acrylic acid = | 315 ppm |
| Hunter Color, HC60, initial = | 69 |
| Hunter Color, HC60, after 30 days @60° C./90% relative humidity = | 48 |
| Hunter Color, b-value, initial = | 4.3 |
| Hunter Color, b-value, after 30 days @60° C./90% relative humidity = | 12.7. |

Comparative Example 5

An aqueous monomer mixture containing 28 wt. % acrylic acid, 0.2 wt. % pentaerythritol triallyl ether based on acrylic acid, 0.20 wt. % sodium persulfate based on acrylic acid, 0.044 wt. % 2-hydroxy-2-methyl-1-phenyl-propan-1-one (DAROCUR® 1173) based on acrylic acid, and 0.022 wt. % 2,2-dimethoxy-1,2-diphenylethan-1-one (IRGACURE® 651) was prepared, then cooled to 15° C. and deoxygenated by bubbling a nitrogen stream through the mixture. Polymerization of the resulting monomer mixture then was initiated by placing the mixture under a UV light (UV intensity=20 mW/cm$^2$) for 25 minutes. The resulting polyacrylic acid gel was extruded through a KitchenAid Model K5SS mixer fitted with a meat grinder attachment. Next, sodium carbonate was added to the hydrogel to adjust the neutralization degree of the acrylic acid groups to 75 mol %, followed by two additional extrusions. The gel was dried at 150° C. for one hour, then milled and sized to 150-850 μm. The dry powder then was surface crosslinked by spraying a solution containing 0.15 wt. % ethylene glycol diglycidyl ether based on powder, 3.35 wt. % water based on powder, and 8.0 wt. % methanol based on powder onto the powder particles, followed by curing at 150° C. for one hour. The properties of the resulting polymer were as follows:

| | |
|---|---|
| CRC = | 29.7 g/g |
| AUL 0.7 psi = | 24.9 g/g |
| Extractables = | 10.0 wt. % |
| Residual acrylic acid = | 260 ppm |
| Hunter Color, HC60, initial = | 59 |
| Hunter Color, HC60, after 30 days @60° C./90% relative humidity = | 38 |
| Hunter Color, b-value, initial = | 9.8 |
| Hunter Color, b-value, after 30 days @60° C./90% relative humidity = | 14.8. |

Comparative Example 6

An aqueous monomer mixture containing 28 wt. % acrylic acid, 0.2 wt. % pentaerythritol triallyl ether based on acrylic acid, 0.066 wt. % 2-hydroxy-2-methyl-1-phenyl-propan-1-one (DAROCUR® 1173) based on acrylic acid, 0.033 wt. % 2,2-dimethoxy-1,2-diphenylethan-1-one (IRGACURE®651), and 0.10 wt. % 2,2'-azobisamidinopropane dihydrochloride was prepared, then cooled to 15° C. and deoxygenated by bubbling a nitrogen stream through the mixture. Polymerization of the resulting monomer mixture then was initiated by placing the mixture under a UV light (UV intensity=20 mW/cm$^2$) for 25 minutes. The resulting polyacrylic acid gel was extruded through a KitchenAid Model K5SS mixer fitted with a meat grinder attachment. Next, sodium carbonate was added to the hydrogel to adjust the neutralization degree of the acrylic acid groups to 75 mol %, followed by two additional extrusions. The gel was dried at 150° C. for one hour and milled, then sized to 150-850 μm. The dry powder then was surface crosslinked by spraying a solution containing 0.15 wt. % ethylene glycol diglycidyl ether based on powder, 3.35 wt. % water based on powder, and 8.0 wt. % methanol based on powder onto the powder particles, followed by curing at 150° C. for one hour. The properties of the resulting polymer were as follows:

| | |
|---|---|
| CRC = | 30.4 g/g |
| AUL 0.7 psi = | 23.5 g/g |
| Extractables = | 12.4 wt. % |
| Residual acrylic acid = | 5870 ppm |
| Hunter Color, HC60, initial = | 76 |
| Hunter Color, HC60, after 30 days @60° C./90% relative humidity = | 68 |
| Hunter Color, b-value, initial = | 3.5 |
| Hunter Color, b-value, after 30 days @60° C./90% relative humidity = | 5.3. |

Example 2 and Comparative Examples 4-6 each are post-neutralization polymerizations, and, similar to Example 1 and Comparative Examples 1-3, illustrate unexpected benefits provided by the present invention. Example 2 and Comparative Examples 4-6 show the good initial color and color stability provided when a sulfinic acid derivative is used as the reducing agent of a redox initiator. In particular, color degradation in Comparative Examples 4 and 5 was observed after storing the SAP at 60° C. and 90% relative humidity for 30 days. Comparative Example 5 also exhibits a relatively poor initial color. Comparative Example 6 exhibited an unacceptable level of RAA for commercial applications and a substantial increase in extractables compared to Example 2.

Example 3

A 10 L capacity polyethylene vessel, well insulated by foamed polymer material, was charged with 3400 g of demineralized water and 1400 g of acrylic acid. N,N'-methylenbisacrylamide (2.8 g) then was added as copolymerization crosslinker. At a temperature of 10° C., 2.2 g of 2,2'-azobisamidinopropane dihydrochloride, dissolved in 25 g of demineralized water, and 0.28 g of hydrogen peroxide, dissolved in 150 g of demineralized water, were added in succession, and the mixture was stirred. The resulting solution then was deoxygenated by bubbling a nitrogen stream through the solution for 30 minutes, followed by the addition of 0.2 g of a mixture containing 50-60% 2-hydroxy-2-sulfinatoacetic acid, disodium salt, 30-35% of sodium sulfite and 10-15% of 2-hydroxy-2-sulfonatoacetic acid, disodium salt (BRUGGOLITE® FF6), dissolved in 25 g of demineralized water. The reaction solution then was allowed to stand without stirring, and the temperature of the polymerization rose to about 96° C. A solid gel was obtained, and the gel subsequently was comminuted mechanically. Next, a 50% strength by weight sodium hydroxide solution was added to the hydrogel to adjust the neutralization degree of the acrylic acid groups to 74 mol %, followed by two additional extrusions. The gel then was dried, ground, and classified to a particle size distribution 106-850 μm. One kilogram of the dried hydrogel then was sprayed in a plowshare mixer with a solution containing 25 g demineralized water, 25 g propylene glycol, and 2.0 g N,N,N',N'-tetrakis(2-hydroxyethyl)adipamide (PRIMID XL-522, commercially available from Ems-Chemie AG), then the mixture was heated at 165° C. for 2 hours. The properties of the resulting polymer were as follows:

| | |
|---|---|
| CRC = | 28.4 g/g |
| AUL 0.7 psi = | 26.8 g/g |
| Extractables = | 4.3 wt. % |
| Residual acrylic acid = | 220 ppm |
| Hunter Color, HC60, initial = | 73 |
| Hunter Color, HC60, after 30 days @60° C./90% relative humidity = | 65 |
| Hunter Color, b-value, initial = | 6.2 |
| Hunter Color, b-value, after 30 days @60° C./90% relative humidity = | 7.4. |

Comparative Example 7

A 10 L capacity polyethylene vessel, well insulated by foamed polymer material, was charged with 3400 g of demineralized water and 1400 g of acrylic acid. N,N'-methylenbisacrylamide (2.8 g) added as copolymerization crosslinker. At a temperature of 10° C., 2.2 g of 2,2'-azobisamidinopropane dihydrochloride, dissolved in 25 g of demineralized water, and 3.5 g of sodium persulfate, dissolved in 150 g of demineralized water, were added in succession and the mixture was stirred. The resulting solution then was deoxygenated by bubbling a nitrogen stream through the solution for 30 minutes, followed by the addition of 0.2 g of ascorbic acid, dissolved in 25 g of demineralized water. The reaction solution then was allowed to stand without stirring, and the temperature of the polymerization rose to about 94° C. A solid gel was obtained, and the gel subsequently was comminuted mechanically. Next, a 50% strength by weight sodium hydroxide solution was added to the hydrogel to adjust the neutralization degree of the acrylic acid groups to 74 mol %, followed by two additional extrusions. The gel then was dried, ground and classified to a particle size distribution 106-850 μm. One kilogram of the dried hydrogel then was sprayed in a plowshare mixer with a solution containing 25 g demineralized water, 25 g propylene glycol, and 2.0 g N,N,N',N'-tetrakis(2-hydroxyethyl)adipamide (PRIMID XL-522), and the mixture was heated at 165° C. for 2 hours. The properties of the resulting polymer were as follows:

| | |
|---|---|
| CRC = | 28.2 g/g |
| AUL 0.7 psi = | 24.9 g/g |
| Extractables = | 6.5 wt. % |
| Residual acrylic acid = | 180 ppm |
| Hunter Color, HC60, initial = | 67 |
| Hunter Color, HC60, after 30 days @60 C./90% relative humidity = | 34 |
| Hunter Color, b-value, initial = | 6.4 |
| Hunter Color, b-value, after 30 days @60° C./90% relative humidity = | 14.1. |

Example 3 and Comparative Example 7 are postneutralization polymerizations and demonstrate the improvement in HC60 and b-value after storage at 60° C. and 90% relative humidity for 30 days when a sulfinic acid derivative is utilized as the reducing agent of a redox initiator system.

Example 4

Acrylic acid (92.4 g), 0.026 g trimethylolpropane triacrylate, and 87.2 g demineralized water were admixed. Sodium carbonate (40.4 g) then was added, and the temperature of the monomer solution was maintained below 30° C. during this neutralization reaction. Then, 0.081 g 2,2'-azobisamidinopropane dihydrochloride and 0.054 g hydrogen peroxide were admixed into the monomer mixture. The monomer mixture then was heated to 62° C. and poured into a pan. Next, a mixture (0.027 g) containing 50-60% of 2-hydroxy-2-sulfinatoacetic acid, disodium salt, 30-35% of sodium sulfite and 10-15% of 2-hydroxy-2-sulfonatoacetic acid, disodium salt (BRUGGOLITE® FF6), dissolved in 5 g of demineralized water, was added to initiate the polymerization. Due to the heat of polymerization, the major part of the water evaporated during the reaction, and at the end of the polymerization, a polymer mass having a residual moisture content of about 15 wt. % was obtained. The polymer mass was dried in a drying oven at 120° C., milled, and classified to a particle size distribution 106-850 μm. The dry powder then was surface crosslinked by spraying a solution containing 0.12 wt. % ethylene glycol diglycidyl ether based on powder, 3.35 wt. % water based on powder, and 1.65 wt. % isopropanol based on powder onto the powder particles, followed by curing at 150° C. for one hour. The properties of the resulting polymer were as follows:

| | |
|---|---|
| CRC = | 31.8 g/g |
| AUL 0.7 psi = | 22.6 g/g |
| Residual acrylic acid = | 415 ppm |
| Hunter Color, HC60, initial = | 88 |
| Hunter Color, HC60, after 30 days = @60° C./90% relative humidity | 65 |
| Hunter Color, b-value, initial = | 1.8 |
| Hunter Color, b-value, after 30 days = @60° C./90% relative humidity | 4.8. |

Example 5

Acrylic acid (92.4 g), 0.026 g trimethylolpropane triacrylate, and 87.2 g demineralized water were admixed. Sodium carbonate (40.4 g) was added, and the temperature of the monomer solution was maintained below 30° C. during this neutralization reaction. Then, 0.081 g 2,2'-azobisamidinopropane dihydrochloride, 0.018 g DAROCUR® 1173, and 0.054 g hydrogen peroxide were admixed into the monomer mixture. The monomer mixture was heated to 62° C. and poured into a pan, then a mixture (0.027 g) containing 50-60% 2-hydroxy-2-sulfinatoacetic acid, disodium salt, 30-35% sodium sulfite, and 10-15% 2-hydroxy-2-sulfonatoacetic acid, disodium salt (BRUGGOLITE® FF6), dissolved in 5 g of demineralized water, was added to initiate the polymerization. Due to the heat of polymerization, the major part of the water evaporated during the reaction, and at the end of the polymerization, a polymer mass having a residual moisture content of about 15 wt. % was obtained. The polymer mass was placed under UV light (UV intensity=20 mW/cm$^2$) for 8 minutes, then dried in a drying oven at 120° C., milled, and classified to a particle size distribution 106-850 μm. The dry powder then was surface crosslinked by spraying a solution containing 0.12 wt. % ethylene glycol diglycidyl ether based on powder, 3.35 wt. % water based on powder, and 1.65 wt. % isopropanol based on powder onto the powder particles, followed by curing at 150° C. for one hour. The properties of the resulting polymer were as follows:

| | |
|---|---|
| CRC = | 30.7 g/g |
| AUL 0.7 psi = | 22.9 g/g |
| Residual acrylic acid = | 65 ppm |
| Hunter Color, HC60, initial = | 86 |
| Hunter Color, HC60, after 30 days @60° C./90% relative humidity = | 64 |
| Hunter Color, b-value, initial = | 2.0 |
| Hunter Color, b-value, after 30 days @60° C./90% relative humidity = | 5.2 |

Comparative Example 8

Acrylic acid (92.4 g), trimethylolpropane triacrylate, and 87.2 g of demineralized water were mixed together. Sodium carbonate (40.4 g) was added, and the temperature of the monomer solution was maintained below 30° C. during this neutralization reaction. Then, 0.081 g 2,2'-azobisamidinopropane dihydrochloride and 0.15 g sodium persulfate were admixed into the monomer mixture. The monomer mixture was poured into a pan and heated to 67° C. to initiate the polymerization. Due to the heat of polymerization, the major part of the water evaporated during the reaction, and at the end of the polymerization, a polymer mass having a residual moisture content of about 13 wt. % was obtained. The polymer mass was dried in a drying oven at 120° C., milled, and classified to a particle size distribution 106-850 μm. The dry powder then was surface crosslinked by spraying a solution, containing 0.12 wt. % ethylene glycol diglycidyl ether based on powder, 3.35 wt. % water based on powder, and 1.65 wt. % iso-propanol based on powder onto the powder particles, followed by curing at 150° C. for one hour. The properties of the resulting polymer were as follows:

| | |
|---|---|
| CRC = | 32.3 g/g |
| AUL 0.7 psi = | 20.8 g/g |
| Residual acrylic acid = | 175 ppm |
| Hunter Color, HC60, initial = | 65 |
| Hunter Color, HC60, after 30 days @60° C./90% relative humidity = | 22 |
| Hunter Color, b-value, initial = | 7.9 |
| Hunter Color, b-value, after 30 days @60° C./90% relative humidity = | 14.5 |

Examples 4 and 5 and Comparative Example 8, all preneutralization polymerizations, show that the optional UV dose substantially reduces RAA without adversely affecting initial color or color stability (Examples 4 and 5). Comparative Example 8 shows a poor color stability and low initial b-value when a persulfate is used as a component of the initiator system and a sulfinic acid derivative is omitted (Comparative Example 8 compared to Examples 4 and 5).

Overall, it has been found that essentially eliminating a persulfate, and including 2-hydroxy-2-sulfinatoacetic acid, a sulfinic acid derivative, preferably 2-hydroxy-2-sulfonatoacetic acid, salts thereof, or a mixture thereof as the reducing agent of a polymerization initiator in the monomer mixture, and optionally irradiating the resulting SAP hydrogel with a low dose of UV radiation provides an SAP manufacturing process for a color-stable SAP. The method applies to both preneutralization and postneutralization SAP manufacturing processes. The color-stable SAP maintains a crisp, white color over extended storage periods, including in high temperature and humidity storage conditions.

Many modifications and variations of the invention as hereinbefore set forth can be made without departing from the spirit and scope thereof and, therefore, only such limitations should be imposed as are indicated by the appended claims.

What is claimed is:
1. A method of manufacturing color-stable superabsorbent polymer particles comprising the steps of:
(a) forming a monomer mixture comprising:
(i) at least one monomer capable of forming a superabsorbent polymer,
(ii) a crosslinking agent,
(iii) an initiator system comprising a sulfinic acid derivative having a structure

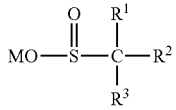

wherein M is hydrogen, an ammonium ion, or a monovalent or a divalent metal ion of groups Ia, IIa, IIb, IVa, and VIIIb of the Periodic Table of the Elements;
$R^1$ is OH or $NR^4R^5$, wherein $R^4$ and $R^5$, independently, are H or $C_1$-$C_6$alkyl;
$R^2$ is H or an alkyl, alkenyl, cycloalkyl, or aryl group, optionally having 1-3 substituents independently selected from the group consisting of $C_1$-$C_6$alkyl, OH, O—$C_1$-$C_6$alkyl, halogen, and $CF_3$; and
$R^3$ is COOM, $SO_3M$, $COR^4$, $CONR^4R^5$, or $COOR^4$, wherein M, $R^4$, and $R^5$ are as defined above, or, if $R^2$ is unsubstituted or unsubstituted aryl, $R^3$ is H;
and the salts thereof;
or a mixture thereof;
(iv) an optional photoinitiator, and
(v) water;
(b) polymerizing the monomer and the crosslinking agent in the monomer mixture to form a superabsorbent polymer hydrogel;
(c) optionally subjecting the superabsorbent polymer hydrogel to a low dose of UV radiation;
(d) comminuting the superabsorbent polymer hydrogel to provide superabsorbent hydrogel particles; and
(e) drying the superabsorbent polymer hydrogel particles for a sufficient time at a sufficient temperature to provide the color-stable superabsorbent polymer particles, wherein the color-stable SAP particles, after storage for 30 days at 60° C. and 90% relative humidity, exhibit an HC60 color value of at least 60 and a maximum b-value of 10.

2. The method of claim 1 wherein optional step (c) is performed prior to step (d).

3. The method of claim 1 wherein step (d) is performed prior to optional step (c).

4. The method of claim 1 wherein the initiator system further comprises a thermal initiator.

5. The method of claim 1 wherein the initiator system comprises hydrogen peroxide as an oxidizing agent.

6. The method of claim 5 wherein the hydrogen peroxide is present in the monomer mixture in a sufficient amount to initiate polymerization and avoid a substantial decrease in superabsorbent polymer absorption properties.

7. The method of claim 1 wherein the sulfinic acid derivative comprises 2-hydroxy-2-sulfinatoacetic acid, a salt thereof, or a mixture thereof.

8. The method of claim 7 wherein the initiator system further comprises 2-hydroxy-2-sulfonatoacetic acid, a salt thereof, or a mixture thereof.

9. The method of claim 1 wherein the initiator system further comprises sodium sulfite.

10. The method of claim 1 wherein the initiator system contains 0 to 500 ppm of a persulfate.

11. The method of claim 10 wherein the initiator system is essentially free of a persulfate.

12. The method of claim 1 wherein the optional photoinitiator is present in the monomer mixture in an amount of about 10 to about 1000 ppm, by weight, of the monomer mixture.

13. The method of claim 1 wherein the optional photoinitiator comprises a compound having a formula

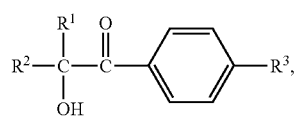

wherein $R^1$ and $R^2$, independently, are $C_{1-3}$alkyl, or are taken together to form a $C_{4-8}$carbocyclic ring, $R^3$ is H, methyl, ethyl, or $(OCH_2CH_2)_nOH$, and n is 1-20.

14. The method of claim 1 wherein the optional photoinitiator comprises hydroxycyclohexyl phenyl ketone, 2,2-dimethoxy-1,2-diphenylethan-1-one,

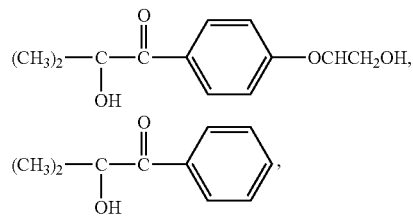

benzoin, a benzoin ether, a benzyl ketal, an acylphosphine oxide, camphorquinone, bisimidazole, a dialkylacetophenone, an α-aminoacetophenone, a chlorinated acetophenone, benzophenone, a benzophenone derivative, p-benzoylbenzyl trimethyl ammonium bromide, a thioxanthone derivative, (3-(3,4-dimethyl-9-oxo-9H-thioxanthen-2-yloxy)-2-hydroxypropyl)-trimethyl ammonium chloride, and mixtures thereof.

15. The method of claim 1 wherein the color-stable superabsorbent polymer particles comprise a polymerized α,β-unsaturated carboxylic acid, or a salt or anhydride thereof.

16. The method of claim 1 wherein the monomer capable of forming the superabsorbent polymer is selected from the group consisting of acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, maleic anhydride, vinylsulfonic acid, allylsulfonic acid, vinyl toluenesulfonic acid, styrenesulfonic acid, sulfoethyl aceylate, sulfoethyl methacrylate, sulfopropyl acrylate, sulfopropyl methacrylate, sulfopropyl acrylate, sulfopropyl methacrylate, 2-hydroxy-3-methacryloxypropyl sulfonic acid, 2-acrylamido-2-methylpropane sulfonic acid, methacryloxy ethyl phosphate, and mixtures thereof.

17. The method of claim 1 wherein the superabsorbent polymer is selected from the group consisting of polyacrylic acid, a hydrolyzed starch-acrylonitrile graft copolymer, a starch-acrylic acid graft copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylphosphonic acid), a poly(vinylphosphoric acid), a poly(vinylsulfuric acid), a sulfonated polystyrene, and salts and mixtures thereof.

18. The method of claim 1 wherein the superabsorbent polymer comprises polyacrylic acid neutralized about 15% to 100%.

19. The method of claim 1 wherein the superabsorbent polymer is selected from the group consisting of a poly(vinylamine), a poly(dialkylaminoalkyl(meth)acrylamide), a polyethylenimine, a poly(allylamine), a poly(allylguanidine), a poly(dimethyldiallylammonium hydroxide), a quaternized polystyrene derivative, a guanidine-modified polystyrene, a quaternized poly(meth)acrylamide) or ester analog, a poly(vinylguanidine), and salts and mixtures thereof.

20. The method of claim 1 wherein the superabsorbent polymer comprises a multicomponent superabsorbent polymer.

21. The method of claim 1 wherein the HC60 color value is at least 63.

22. The method of claim 1 wherein the maximum b-value is 8.

23. The method of claim 1 wherein the color-stable SAP particles have a residual monomer content of 500 ppm or less.

24. The method of claim 1 wherein the monomer comprises acrylic acid, a salt thereof, or a mixture thereof; the initiator system consists essentially of hydrogen peroxide as an oxidizing agent, 2-hydroxy-2-sulfinatoacetic acid, salts thereof, or mixtures thereof as a reducing agent, and a thermal initiator; the optional photoinitiator is present in an amount of 0 to about 1000 ppm, by weight, of the monomer mixture; and the SAP hydrogel is subjected to UV radiation.

25. The method of claim 24 wherein the initiator system further comprises 2-hydroxy-2-sulfonatoacetic acid, sodium sulfite, or a mixture thereof.

26. The method of claim 1 further comprising the step of:
(f) surface treating the color-stable superabsorbent polymer particles.

27. Color-stable superabsorbent particles prepared by the method of claim 1.

28. An absorbent article comprising the color-stable superabsorbent particles prepared by the method of claim 1.

29. The article of claim 28 wherein the article is a diaper or a catamenial device.

30. A diaper having a core, said core comprising at least 10% by weight of the color-stable superabsorbent particles prepared by the method of claim 1.

31. A diaper having a core, said core comprising at least 40% by weight of the color-stable superabsorbent particles prepared by the method of claim 1.

* * * * *